United States Patent [19]
Watanabe et al.

[11] Patent Number: 5,874,701
[45] Date of Patent: Feb. 23, 1999

[54] PHOTOCATALYTIC AIR TREATMENT PROCESS UNDER ROOM LIGHT

[75] Inventors: Toshiya Watanabe; Atushi Kitamura; Eiichi Kojima, all of Kita-kyushu; Kazuhito Hashimoto, Yokohama; Akira Fujishima, Kawasaki, all of Japan

[73] Assignee: Toto Co., Ltd., Japan

[21] Appl. No.: 630,468

[22] Filed: Apr. 10, 1996

Related U.S. Application Data

[63] Continuation of Ser. No. 256,392, filed as PCT/JP93/01598, Nov. 5, 1993, published as WO94/11092, May 26, 1994, abandoned.

[30] Foreign Application Priority Data

Oct. 11, 1992 [JP] Japan ................................. 4-324800

[51] Int. Cl.⁶ .................................................. C07B 63/00
[52] U.S. Cl. .................................. 204/157.15; 204/158.2; 204/158.21; 204/157.3; 588/227; 55/279
[58] Field of Search ........................... 204/157.15, 158.2, 204/158.21, 157.3; 588/227; 55/279; 250/492.1, 492.2

[56] References Cited

U.S. PATENT DOCUMENTS

| | | | |
|---|---|---|---|
| 5,032,241 | 7/1991 | Robertson et al. | 204/157.15 |
| 5,152,814 | 10/1992 | Nelson | 55/270 |
| 5,225,167 | 7/1993 | Wetzel | 422/121 |

FOREIGN PATENT DOCUMENTS

| | | |
|---|---|---|
| 1-139139 | 5/1989 | Japan . |
| 1139139 | 5/1989 | Japan . |
| 3-8448 | 1/1991 | Japan . |
| 4-272337 | 9/1992 | Japan . |
| 4272337 | 9/1992 | Japan . |
| 4-307065 | 10/1992 | Japan . |
| 4-307066 | 10/1992 | Japan . |
| 4307065 | 10/1992 | Japan . |
| 4307066 | 10/1992 | Japan . |

OTHER PUBLICATIONS

H. Kawaguchi, "Photocatalytic Decomposition of Phenol in the Presence of Titanium Dioxide," *Environmental Technology Letters*, vol. 5, pp. 471–474, 1984.

Allen J. Bard, "Photoelectrochemistry and Heterogeneous Photocatalysis at Semiconductors," *Journal of Photochemistry*, Oct. (1979), pp. 59–75.

Akira Fujishima et al, "Electrochemical Photolysis of Water at a Semiconductor Electrode," *Nature*, vol. 238, Jul. 7, 1972, pp. 37–38.

*Primary Examiner*—Cecilia J. Tsang
*Assistant Examiner*—C. Delacroix-Muirheid
*Attorney, Agent, or Firm*—Lorusso & Loud

[57] ABSTRACT

A process for photocatalytically treating a hospital room contaminated by bacteria or an interior environment bearing airborne malodorous substances. A thin film of photocatalyst made of a semiconductor such as titanium dioxide is disposed on the inner wall of the hospital room or living space. The photocatalytic thin film is irradiated by a light source suitable for general lighting applications, such as a fluorescent lamp, and is photoexcited by the small amount of ultraviolet radiation included in the light of fluorescent lamp. The wattage of the fluorescent lamp as well as the distance between the photocatalytic thin film and the lamp are selected such that the intensity of those UV wavelengths which have a higher energy than the band gap energy of the photo-catalyst is 0.001–1 mW/cm², preferably, 0.01–0.1 mW/cm². The bacteria and chemical compounds deposited on the photoexcited thin film are photodecomposed.

24 Claims, 11 Drawing Sheets

PHOTOCATALYTIC AIR TREATMENT PROCESS UNDER ROOM LIGHT

This application is a continuation of application Ser. No. 08/256,392, filed as PCT/JP93/01598 Nov. 5, 1993 published as WO94/11092 May 26, 1994, now abandoned.

TECHNICAL FIELD

The present invention relates to a photocatalytic process for the treatment of an indoor environment contaminated by bacteria and airborne substances.

BACKGROUND ART

Living spaces of residences and offices may carry airborne malodorous substances including sulfur compounds such as hydrogen sulfide and methyl mercaptan, nitrogen compounds such as ammonia, and other compounds such as fatty acid. To provide a comfortable living environment, it is desirable to treat the contaminated air for removal of the malodorous substances. In a medical environment, on the other place, antibiotic medication has induced inadvertent evolution of those bacteria having resistance against antibiotics. Among them, methicillin-resistant *Staphylococcus aureus* (MRSA), for example, has caused a serious problem of nosocomial (i.e., in-hospital) infection.

Accordingly, attention has been drawn toward the use of semiconductive photocatalyst for the purposes of processing the environment contaminated by bacteria and malodorous substances.

Since one of the inventors of the present invention and his coworker have reported their investigation on photoelectrolytic process of water (known as the "Honda and Fujishima effect") in a photoelectrochemical cell having a single-crystal semiconductor electrode of titanium dioxide ($TiO_2$) in the form of rutile and a counter electrode of platinum (Nature, vol. 238(1972), 37–38), many researches have been carried out on the treatment of various media with a semiconductive photocatalyst.

To briefly set out the principle of the photocatalytic process in a photoelectrochemical cell with reference to FIG. 1 of the accompanying drawings, when a semiconductor photocatalyst is illuminated and is caused to absorb the light energy (hv) higher than the band gap energy (Eg) of the semiconductor, the electrons in the valance band are photoexcited and raised into the conduction band to produce electron-hole pairs ($e^- - h^+$) at the surface layer of the semiconductor.

$$hv \rightarrow e^- + h^+$$

In order for the thus generated electrons and holes to contribute in the photoelectrolysis of water, they must be moved, respectively, to separate oxidation and reduction sites that are spaced from each other (charge separation). Otherwise, the electrons and holes would recombine and convert into thermal energy without contributing in the redox process.

In a photoelectrochemical cell wherein a semiconductor-electrolyte junction is present, charge separation is carried out in the following manner. Thus, as the semiconductor is brought into contact with the electrolyte, transfer of charges occurs until the Fermi levels in both phases become equal. As a result, in the n-type semiconductor such as $TiO_2$, the semiconductor surface is positively charged. The electric field developed by the charges causes a bending of the bands in the space charge region near the semiconductor surface as shown in FIG. 1. The electrons in the conduction band and the holes in the valance band are separated by the band bending, with the electrons $e^-$ moving to the bulk and the holes h+ moving to the surface of the semiconductor. The holes $h^+$ moved to the semiconductor surface oxidize water to generate hydrogen $$2h^+ + H_2O \rightarrow \tfrac{1}{2}O_2 + 2h^+$$

whereas the electrons $e^-$ transferred via the lead wire to the metallic counter electrode reduce water to produce hydrogen $$2e^- + 2H^+ \rightarrow H_2$$

Since the success of the photoelectrolytic process of water in the photoelectrochemical cell has been published, A. J. Bard reported that, not only the photoelectrochemical cell having a single-crystal semiconductor electrode, platinized $TiO_2$ powders also function as the photoelectrochemical cell (Journal of Photochemistry, 10(1979), 59–75). A. J. Bard considers that a platinized $TiO_2$ particle functions as a short-circuited photoelectrochemical cell.

Thereafter, it has been found that even bare $TiO_2$ particles present a photocatalytic effect and various investigations and researches have been made on the photocatalytic decomposition of ammonia, carboxylic acid, phenol and other compounds (e.g., H. Kawaguchi, Environmental Technology Letters, vol. 5, pp 471–474).

In this regard, it is believed that, in the photocatalytic decomposition of compounds, holes $h^+$ and electrons $e^-$ generated by photoexcitation of semiconductor photocatalyst serve to oxidize and reduce surface hydroxyl group and surface oxygen, respectively, to generate OH radical ($\cdot OH$) and superoxide ion ($O_2^-$)

$$OH^- + h^+ \rightarrow \cdot OH$$

$$O_2 + e^- \rightarrow O_2^-$$

These species are highly active and induce redox process of the compounds. It is considered that photodecomposition of a compound is a multiple electron process. Thus, the original species is transformed through a plurality of intermediates into final products.

Turning to the prior art, it has been considered that, to photoexcite a photocatalyst to provoke a photocatalytic process, it is desirable to use ultraviolet radiations of a high light energy and to irradiate them at as high a light intensity as possible. For example, Japanese Patent Kokai Publication No. 2-280818 proposes a process of deodorizing air wherein UV radiations having a wave length of 250 nm are irradiated at an intensity greater than 2 $mW/cm^2$ to excite a photocatalyst. Similarly, Japanese Patent Kokai Publication No. 63-267867 discloses a deodorizer device wherein UV radiations having a wave length of 250 nm issued from a germicidal lamp are irradiated on the photocatalyst. It will be noted, however, that UV radiation having such a short wave length of 250 nm is harmful to human bodies so that, under UV irradiation, it is necessary to wear protective glasses. Therefore, the prior art process is not directly applicable to a living environment so that the living spaces must be shielded against the UV light source. Furthermore, to strengthen the UV intensity, the light source must be located sufficiently close to the photocatalyst. This limits the surface area of irradiation. Another disadvantage is that expensive germicidal lamps made of quartz glass tube permeable to UV light of 250 nm wave length are required.

In Japanese Patent Kokai Publication No. 4-307066, there is disclosed a deodorizer system wherein UV radiation having a wave length of less than 410 nm is illuminated on a panel coated with photocatalyst. This system is designed such that the light source is shielded from the indoor space because the intensity of UV light is so high. Consequently, the system cannot be applied to sterilization of an exposed surface, such as the interior wall of a care room of a hospital, which may be accessed by people. Moreover, a special purpose light source for photoexciting the photocatalyst must additionally be provided.

DISCLOSURE OF THE INVENTION

The object of the present invention is to provide a photocatalytic process for treating an indoor environment contaminated by bacteria and airborne particulate or volatile substances which may be carried out without resort to a light source which is harmful to human beings.

Another object of the invention is to provide a photocatalytic treatment process which is suitable to effectively sterilize the interior walls of a living space such as a hospital room.

A still another object of the invention is to provide a photocatalytic treatment process which does not necessitate the use of a special light source for excitation of a photocatalyst.

A further object of the invention is to provide a photocatalytic treatment process which is adapted to induce the required photocatalysis with a minimum of electric power consumption.

Another object of the invention is to provide a photocatalytic treatment process which does not interfere with or hinder daily use, appearance and ornamentation of a room.

According to the present invention, there is provided a process for photocatalytically treating an indoor environment or air which is contaminated by bacteria and particulate or volatile substances.

The first feature of the photocatalytic process according to the invention is that a photocatalyst which is in the form of a thin film of a solid-state semiconductive material is provided on at least a part of the interior wall of an indoor space to ensure that the interior wall itself is utilized to provide a reaction surface for photocatalysis. When bacteria and/or airborne substances are brought in contact with the photoexcited thin-film photocatalyst, they are photodecomposed in situ.

As in this manner the inner wall of the indoor space is lined with the thin film of photocatalyst to cause the inner wall per se to provide the reaction surface, the thin film of photocatalyst can be exposed directly to the room. This is particularly advantageous when the process according to the invention is carried out for the purposes of sterilization. Because any bacteria would be killed in situ by the action of photocatalyst, upon contact with the wall surface lined with the photocatalytic thin film, bacterial infection via wall surface contagion can be effectively prevented.

The room lined with the thin film of photocatalyst may also be regarded as a large photocatalytic reactor. Therefore, a photocatalytic reaction surface having as large a surface area as required for photocatalytic decomposition can be readily secured so as to induce an adequate amount of photocatalysis. In addition, in contrast to the conventional suspended particulate system wherein a reaction vessel equipped with a fluid transfer device and agitation device is required, the thin film system according to the invention does not necessitate installation of such a separate reaction vessel. Instead, the thin film of photocatalyst may be readily provided on the inner walls of the indoor spaces.

The second feature of the treatment process according to the invention resides in that the photocatalyst is excited by making use of an electric lamp for general lighting applications (hereinafter general-application lamp), such as a fluorescent lamp, which is provided in a room. To this end, the thin film of photocatalyst is disposed within the range of irradiation of the general-application electric lamp. The commercial general-application electric lamps are safe and harmless since they are primarily designed to cut off harmful UV radiations having a wave length of less than 300 nm. For example, low-pressure mercury lamps intended for general lighting applications, such as fluorescent lamps, are adapted to convert harmful UV rays, which are emanating from mercury atoms excited by electric discharge and which have an intrinsic wave length of about 254 nm, into visible light rays by way of photoluminescence of a fluorescent substance. However, the light radiating from the general-application electric lamp such as fluorescent lamp includes at least a small amount of UV radiation of a wave length range having the light energy higher than the band gap energy of the semiconductor photocatalyst. Therefore, the general-application electric lamp may be used for the purpose of photoexcitation of the photocatalyst, in addition to its intended original purpose of interior illumination.

Since in this manner the photocatalyst is photoexcited by a light source implemented by a general-application electric lamp, there is no need for a separate UV light source for excitation of the photocatalyst. Advantageously, the light source is utilized in two ways for room illumination as well as for photoexcitation of the photocatalyst. In addition, as the light of a general-application electric lamp is exempt from harmful UV radiations, the living region need not be shielded against the light source as in the prior art. Accordingly, the thin film of photocatalyst may be exposed to a room for the purposes of sterilization as described hereinbefore to ensure that the photocatalytic thin film be disposed on a wall surface at whichever locations people are apt to access.

The third feature of the invention is related to the quantum yield of the light energy absorbed by the semiconductor photocatalyst, i.e., the ratio between the number of photons absorbed by the photocatalyst and the number of molecules undergone photoelectrochemical reaction. According to the invention, the wattage of the general-application electric lamp and the distance between the photocatalytic thin film and the lamp are so selected that the total incident light intensity of UV radiations having an energy higher than the band gap energy of the semiconductor photocatalyst is 0.001–1 mW/cm$^2$, preferably, 0.01–0.1 mW/cm$^2$.

This feature is based upon a finding that, in a photocatalytic system wherein a photocatalyst in the form of a thin film is employed and wherein, therefore, a solid-to-gas contact is present, the quantum yield of the light energy increases with decreasing UV intensity. More specifically, according to the experiments conducted by the present inventors, it has been found that, in a thin film photocatalytic system, the quantum efficiency of the light energy absorbed by the photocatalyst increases in response to the decrease in the UV light intensity, as described later in more detail with reference to the accompanying drawings. Although the reasons thereof are not clear, this may probably be explained as follows. Thus, photocatalytic decomposition of a compound is a multiple electron process and, therefore, the speed of decomposition is controlled by the rate-determining step. Contrary to the particulate or powder system wherein a large surface area is available, the thin film system has a limited surface area so that the probability of the photo-generated electrons and holes to reach the reaction sites on the surface of the thin film within the life time thereof is quite small. Accordingly, in a thin film system, the photodecomposition process is highly susceptible to the restraint by the rate-determining step. When the rate-controlling step in the photoelectrochemical reaction reaches a steady state condition, any excessive electrons and holes once produced by photoexcitation of the photocatalyst would undergo recombination before inducing redox process at the reaction sites on the semiconductor surface and would be changed into heat. It is considered that, for these reasons, the lower the UV light intensity (photon density) becomes, the greater the the quantum yield of respective photons becomes.

Since in the process according to the invention a photocatalyst in the form of a thin film is employed and because such a thin film photocatalyst presents an increasing quantum efficiency with decreasing UV intensity, general-application electric lamps, such as fluorescent lamps, of limited UV intensity, may advantageously be used to photoexcite the photocatalyst.

In this regard, as mentioned hereinbefore, an illuminated room lined with the photocatalytic thin film may be regarded as a photocatalytic reaction vessel of the batch type wherein the inner walls thereof act as the photocatalytic reaction surface. To discuss the relationship among the size of the reaction vessel, the total surface area of the reaction and the light intensity on the assumption that the light source is of a given output, as the size of the vessel is increased so that the distance between the light source and the photocatalytic reaction surface is in turn increased, the total surface area available for the installation of the photocatalytic thin film will be increased in proportion to the increase in the distance. However, the light intensity per unit surface area of the thin film will be decreased, presumably in inverse proportion to the square of the distance. On the contrary, when the size of the reaction vessel is reduced, the area of the reaction surface will be decreased while the light intensity on that surface increases generally in inverse proportion to the square of the distance. It will be noted that the number of photons which effectively contribute to the photocatalytic process without suffering electron-hole recombination is proportional to the product of the quantum yield multiplied by the light intensity (photon density) multiplied by the surface area of the thin film. In light of the finding of the present inventors that the quantum yield of the light energy absorbed by the photocatalytic thin film increases with decreasing light intensity, the reaction yield of the reaction vessel as a whole will be enhanced by irradiating a weak UV light upon a broader surface area of the photocatalytic thin film, rather by irradiating a strong UV light energy on a narrower area. However, since the light intensity decreases in inverse proportion to the square of the distance, the reaction yield of the vessel as a whole would be decreased if the distance between the light source and the photocatalyst is set too large. Optimum yield of photocatalysis performed by a room as a whole that functions as a photocatalytic reaction vessel will be attained by setting the wattage of the light source and the distance between the photocatalytic thin film and the light source such that the UV light intensity is 0.001–1 mw/cm$^2$.

Should the output of the light source and the distance be otherwise determined in such a manner that the UV light intensity is greater than 1 mW/cm$^2$, then the chance of electron-hole recombination would be increased so that the high electric power consumption would not be worthwhile from the view point of efficiency of photoexcitation of the photocatalyst and that the intensity of visible light illumination and the amount of heat dissipation would be excessive. If the UV light intensity is less than 0.001 mW/cm$^2$, the decomposition yield of the room would be insufficient.

In this manner, in a thin film system, a high efficiency is attainable by the use of a light source of a rather small UV intensity. According to the invention, therefore, the photocatalyst is advantageously photoexcited by weak UV energy available from the general-application electric lamps such as fluorescent lamps to effectively induce photocatalysis with a minimum electric power consumption.

Preferably, the thin film of photocatalyst is made from powders of titanium dioxide (TiO$_2$). TiO$_2$ is a chemically stable, harmless and non-toxic material which advantageously exhibits a suitable band characteristics for redox process of substances and presents a high photocatalytic activity. It is preferable to use the anatase form of TiO$_2$, while rutile form TiO$_2$ metallized with copper, silver, platinum or other metals may also be used. Also, photocatalytic thin film may be made from another semiconductor material such as WO$_3$, CdS, SrTiO$_3$, or MoS$_2$.

The photocatalytic thin film of TiO$_2$ may be supported on a ceramic substrate such as a tile. In this case, by applying a TiO$_2$ sol on a glazed tile followed by firing at a temperature above the softening point of the glaze, the powders of TiO$_2$ are sintered with each other and are firmly bonded to the glaze, whereby a rigid sintered thin film of TiO$_2$ having a high wear resistivity is obtained. The tiles with the TiO$_2$ thin film thus supported thereon may be readily affixed on the interior walls of a room. Preferably, the thickness of the thin film is 0.3–10 μm. With a greater thickness, the strength of the thin film would be lowered due to shrinkage during sintering so that the thin film would be vulnerable to abrasion. With a thickness less than 0.3 μm, photocatalytic activity would be inadequate.

The thin film of photocatalyst may also be provided by fixing the TiO$_2$ powders on a substrate of ceramics, wood, metal, plastics or other material by way of an inorganic binder such as water glass and alkoxide or an organic binder such as a fluorocarbon polymer.

The light source for photoexciting the photocatalytic thin film may be selected from various commercially available general-application electric lamps depending on the desired intensity of visible and UV light. For example, white light fluorescent lamps, pink light fluorescent lamps and incandescent lamps are suitable when the photocatalytic thin film is to be irradiated at a low UV intensity. With a blue light fluorescent lamp, an increased UV light is obtainable. If the UV intensity is to be increased further, black light fluorescent lamp and black light blue fluorescent lamp having a major wave length of 350–360 nm would be appropriate. In the event that the visible light is to be intensified, a high intensity discharge (HID) lamp such as a metal halide lamp can be used.

The photocatalytic process of the invention may be applied to sterilization and antibacterial treatment of medical facilities such as care rooms and operation rooms of hospitals, antibacterial treatment and deodorization of living spaces such as residences and offices, sterilization and antibacterial treatment of food processing factories and catering facilities, and cleansing of toilet floor and kitchens.

The foregoing principle and features of the invention as well as other features thereof will become apparent in more detail from the following description made with reference to the accompanying drawings.

BEST MODE FOR CARRYING OUT THE INVENTION

Figure 2:
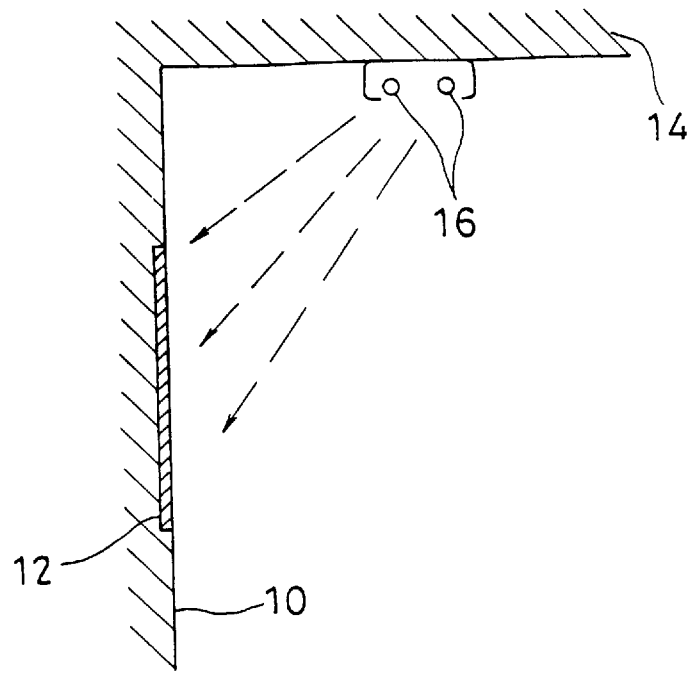
FIGS. 2–5 represent various layouts of light source and photocatalyst.

In FIGS. 2–5, there are shown by way of example various layouts of illumination light source and photocatalyst. In the layout of FIG. 2, the side wall 10 of a room is provided with a panel 12 on which a thin film of photocatalyst is supported, whereas the ceiling 14 is equipped with commercial interior lighting fluorescent lamps 16 to irradiate the photocatalytic panel 12 to thereby excite the photocatalyst for the purpose of deodorization of the ambient air and antibacterial treatment of the side wall.

Figure 3:
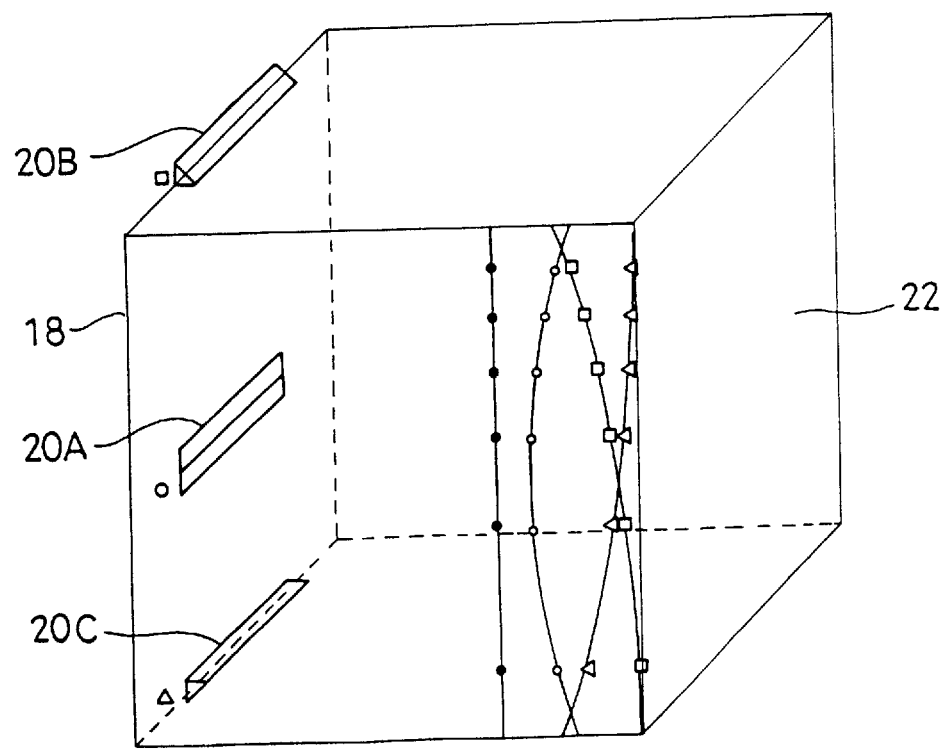

FIG. 3 illustrates a layout adapted to illuminate the photocatalyst at a uniform light intensity. In this layout, one side wall 18 of the room is equipped with three sets of recessed lighting fixtures 20A–20C each incorporating fluorescent lamps, not shown, with the opposite side wall 22 being provided with one or more photocatalytic panels, not shown. The central lighting fixture 20A is directed generally horizontally, with the upper and lower fixtures 20B and 20C being directed, respectively, toward the ceiling and the floor. In FIG. 3, the light intensity distributions obtained by different lighting fixtures are plotted by circular, rectangular and triangular indicia, respectively. It will be understood from the line plotted by the black dots that, in this layout, the sum of the light intensity provided by the three sets of lighting fixtures 20A–20C becomes uniform along the side wall.

Figure 4:
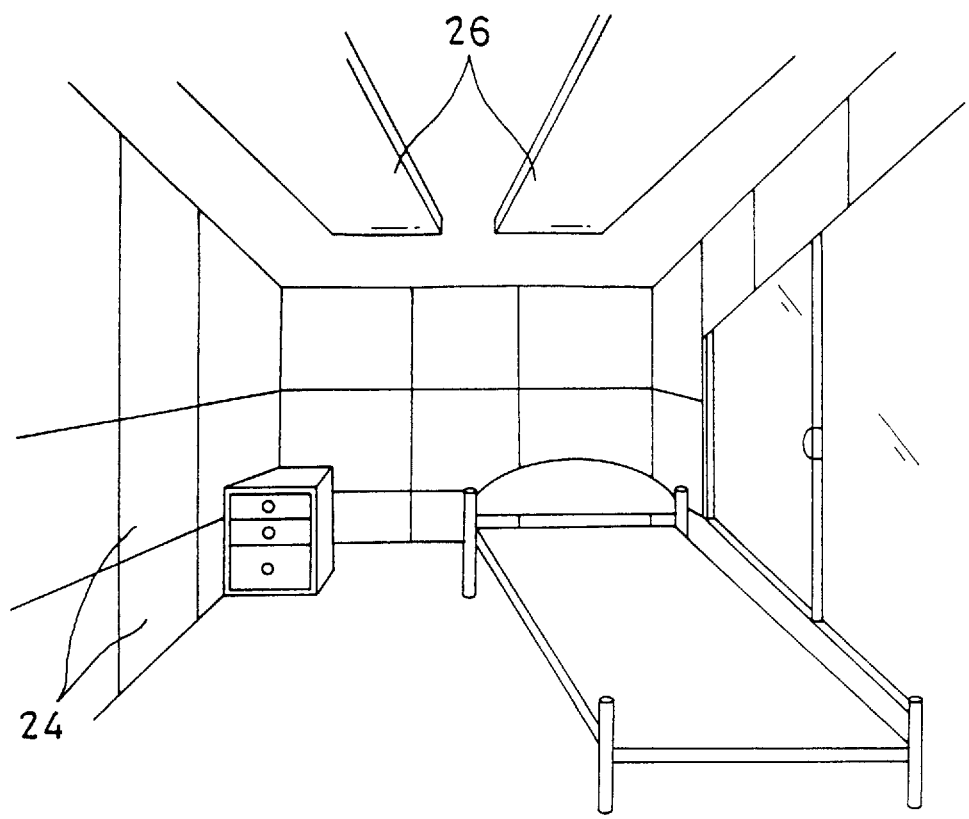

FIG. 4 shows a layout for sterilizing the side walls and the ambient air of a hospital room by way of the process according to the invention. The walls of the care room are covered by tiles 24 supporting the thin film of photocatalyst and the conventional lighting fixtures 26 incorporating fluorescent lamps are disposed on the ceiling of the room.

Figure 5:
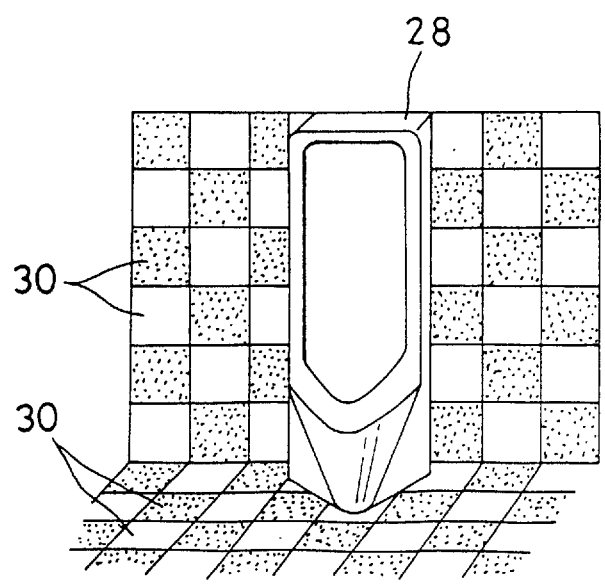
Figure 7C:
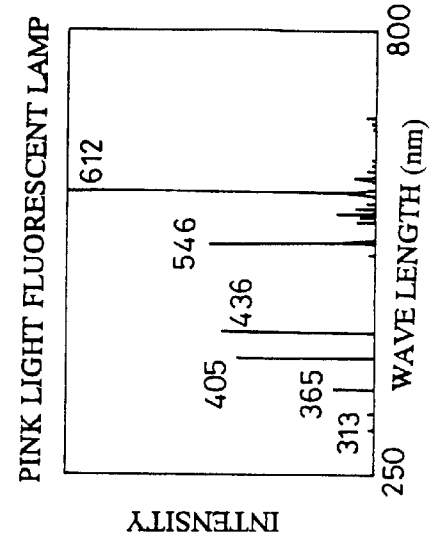
FIGS. 7A–7D are graphs showing spectrum distribution of various commercial fluorescent lamps.
Figure 7D:
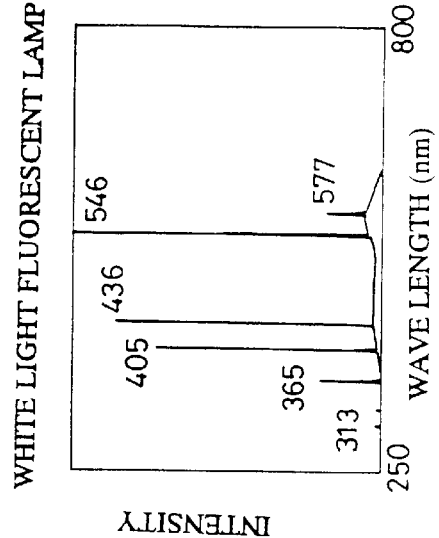
Figure 7A:
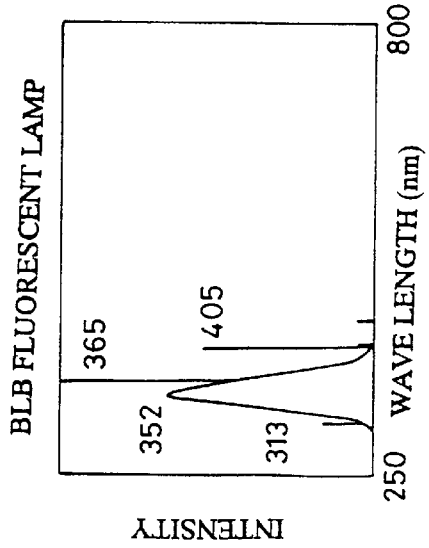
Figure 7B:
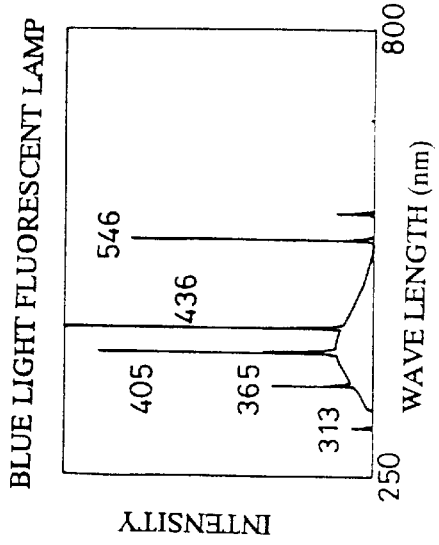

FIG. 5 illustrates another layout wherein an environment, such as a toilet, which is subject to fouling and spoiling is kept clean by photo-decomposition of malodorous substances and splashed soiling substances. The tiles 30 disposed on the wall and floor near the urinal 28 are covered by photocatalytic thin film and are adapted to be subjected to UV irradiation from the conventional lighting fixtures, not shown. The photocatalytic thin film may be affixed directly on sanitary earthenware such as the urinal 28, toilet stool and wash basin for disinfection of bacteria and prevention of dirty deposits.

Figure 1:
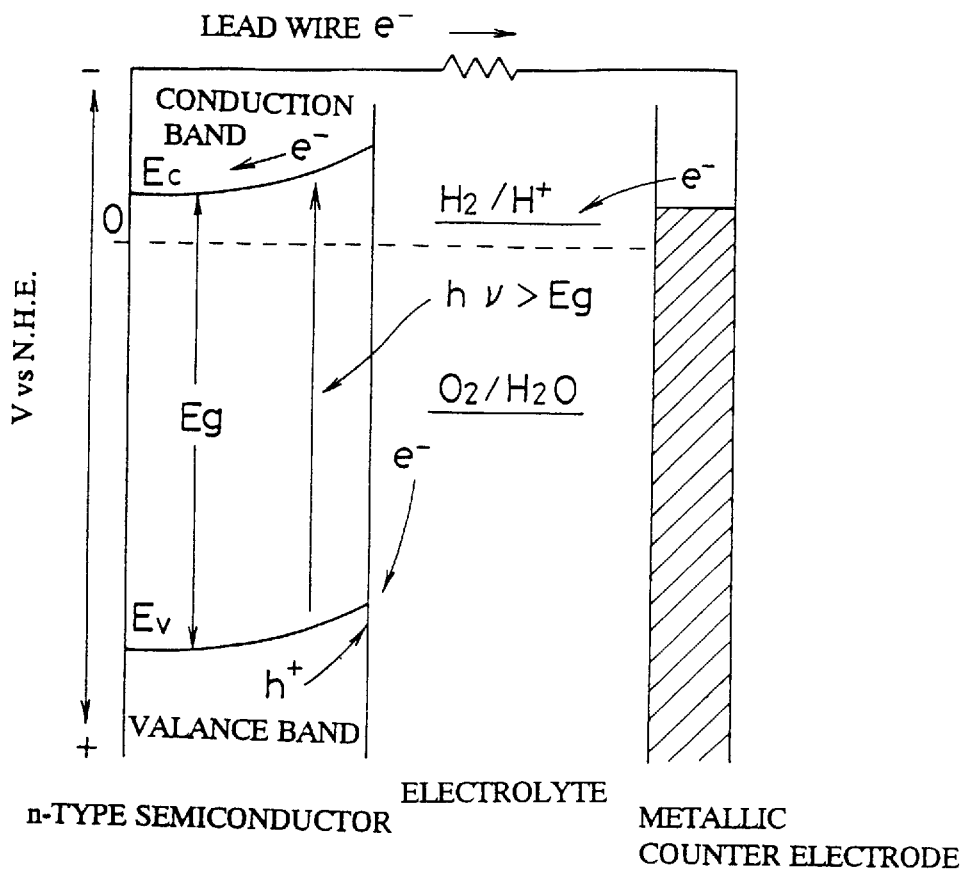
FIG. 1 is a schematic representation illustrating the principle of the semiconductor photocatalyst.
Figure 6:
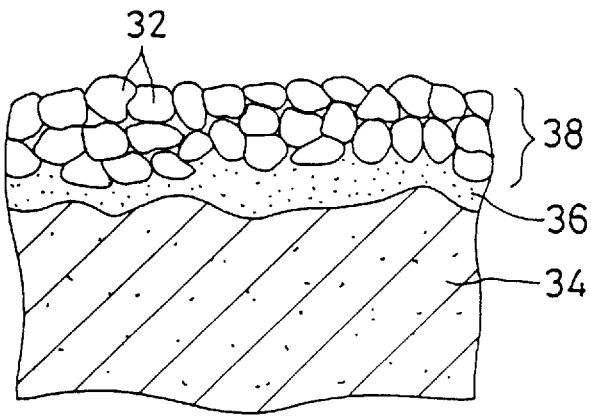
FIG. 6 is a cross-sectional view on a microscopically enlarged scale of a portion of a tile provided with a photocatalytic thin film.

The panel 12 and tiles 24 and 30 on which the thin film of photocatalyst is supported may be manufactured by fixing $TiO_2$ powders on the conventional glazed tiles. Preferably, $TiO_2$ powders are powders of anatase form of $TiO_2$ which has a band gap energy of about 3.2 eV and, accordingly, can be photoexcited by UV radiations having a wave length shorter than 387 nm. A suitable example of anatase form $TiO_2$ powders is $TiO_2$ sol (4% aqueous solution of ammonia; average particle size of 10 nm) marketed by K.K. Taki Chemical (Kakogawa-shi, Hyogo-ken, Japan). The thin film of $TiO_2$ may be formed by spray coating the $TiO_2$ sol on a prefabricated conventional glazed tile and by firing at a temperature of 780° C. which is slightly lower than the brookite (or rutile) transformation point of $TiO_2$. When fired at such temperature, anatase $TiO_2$ particles 32 are sintered with each other and are bonded to the molten glaze 36 at the surface of the tile substrate 34 as shown in FIG. 6 to form a rigid thin film 38 when cooled. Similarly, in the case that the sanitary earthenware such as the urinal 28 per se is to be coated by the photocatalytic thin film, the $TiO_2$ sol may be spray coated on the previously prepared glazed sanitary earthenware, followed by firing.

The light source for photoexcitation of the photocatalyst as well as for room illumination may be selected from various commercially marketed electric lamps for general lighting applications according to the desired luminous intensity of visible and UV light. In FIGS. 7A–7D, there are shown spectrum distribution of the conventional black light blue (BLB) fluorescent lamp, blue light fluorescent lamp, pink light fluorescent lamp and white light fluorescent lamp, respectively, which are usable in the present invention. It will be noted that the light of respective fluorescent lamps includes a small amount of UV light having the wave lengths of 313 nm and 365 nm that correspond to the line spectrum of mercury. However, UV light of less than 300 nm wave length that is harmful to human bodies is never or almost never included. As the UV light of the wave lengths of 313 nm and [36]5 nm have an optical energy higher than the band gap energy of the anatase form $TiO_2$, which band gap energy is equivalent to the wave length of 387 nm, it can be used to photoexcite the photocatalyst comprising anatase form $TiO_2$. The BLB fluorescent lamp emitting a large amount of UV light having a major wave length of 352 nm may advantageously be employed in a situation in which the UV light intensity must be strengthened. Because of low UV light intensity, pink light and white light fluorescent lamps are suitable where the visible light intensity is to be increased to provide a higher degree of room illumination. The light from the blue light fluorescent lamp includes a substantial amount of UV light having light energy higher than the band gap energy of anatase. These fluorescent lamps mentioned above may be used solely or in combination with other fluorescent lamps and other types of electric lamp.

Throughout the various layouts shown in FIGS. 2–5, the distance between the lighting fixtures and the photocatalytic thin film as well as the wattage of the lighting fixtures are determined in such a manner that the light intensity of UV light having light energy higher than the band gap energy of photocatalyst is 0.001–1 $mW/cm^2$, preferably, 0.01–0.1 $mW/cm^2$. The power of the room light utilized for photocatalytic excitation may also be determined taking into account the UV energy of the solar light which may shine into the room during the day time.

As the light source is turned on so that the thin film 38 of photocatalyst is photoexcited by the UV light, the surface hydroxyl groups are oxidized into OH radical ($\cdot$OH) and the surface oxygen reduced into superoxide ions ($O_2^-$) due to the redox action of generated electrons and holes. As these species are highly active, substances or bacteria brought into contact with the surface of the thin film 38 are decomposed or killed. In this regard, it is considered that bacteria such as *Escherichia coli, Pseudomonas aeruginosa* and Staphylococcus are killed because protein forming the cell membrane thereof is chemically decomposed by these active species whereby the cell membrane is physically destroyed.

EXAMPLE 1

The afore-mentioned $TiO_2$ sol marketed from K.K. Taki Chemical was spray coated on an alumina substrate (about 10×10 cm) of about 96% alumina prepared by Nippon Carbide Industries Co., Inc. and the substrate was fired at 780° C. to produce a tile on which is formed a thin film of anatase form $TiO_2$ having a thickness of about 1 $\mu$m. The porosity of the $TiO_2$ thin film was about 40% and the specific surface area thereof was 17.5 $m^2/g$.

Figure 8:
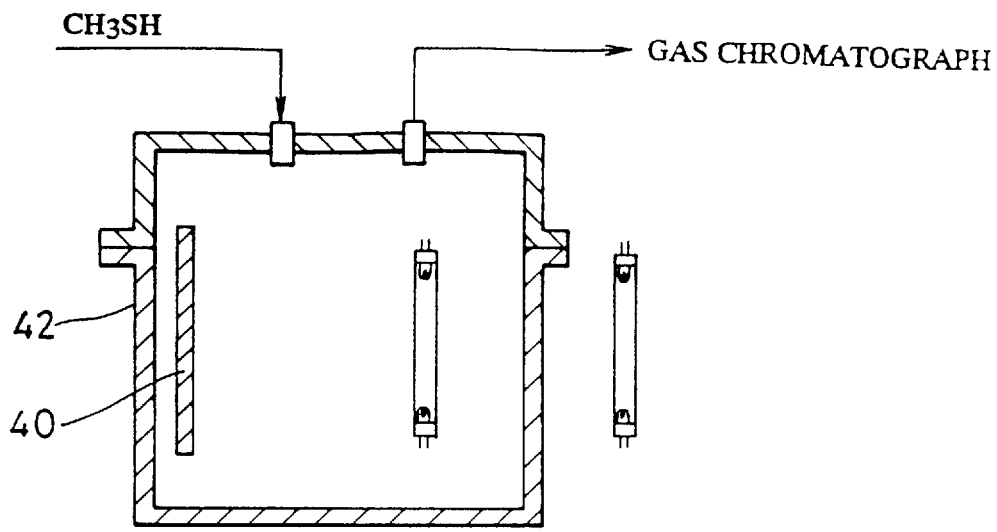
FIG. 8 is a schematic cross-sectional view of an apparatus used in the experimental examples of the invention.

The tile 40 thus fabricated was placed in an 11-litre desiccator 42 made of UV permeable quartz glass, as shown in FIG. 8, and was photoexcited by various light sources under UV radiations of varying intensity for testing the decomposition capability thereof against methyl mercaptan ($CH_3SH$) being one of the malodorous substances. In each run, either about 0.5 or 2 litres of nitrogen gas containing 100 ppm of methyl mercaptan was introduced into the desiccator. The methyl mercaptan content in the desiccator was about 3–5 ppm or 20 ppm. Inside of or outside of the desiccator, a 20-W pink light fluorescent lamp (made by Toshiba; FL20SPK), a 20-W white light fluorescent lamp (made by Toshiba; FL20SW), a 20-w blue light fluorescent lamp (made by Toshiba; FL20SB), and a 4-W BLB fluorescent lamp (made by Sankyo Electric; FL4BLB) were positioned, respectively, in such a manner that the UV light intensity in the wave length range of 300–390 nm was 8 $\mu W/cm^2$, 11 $\mu W/cm^2$, 48 $\mu W/cm^2$, and 295 $\mu W/cm^2$, respectively. For a higher UV intensity of 2–20 $mW/cm^2$, a 200-W mercury xenon lamp (made by Yamashita Denso; SUN-CURE 202) was used while adjusting the output. Gas in the desiccator was periodically sampled for measurement of methyl mercaptan content by way of a gas chromatograph.

Figure 9:
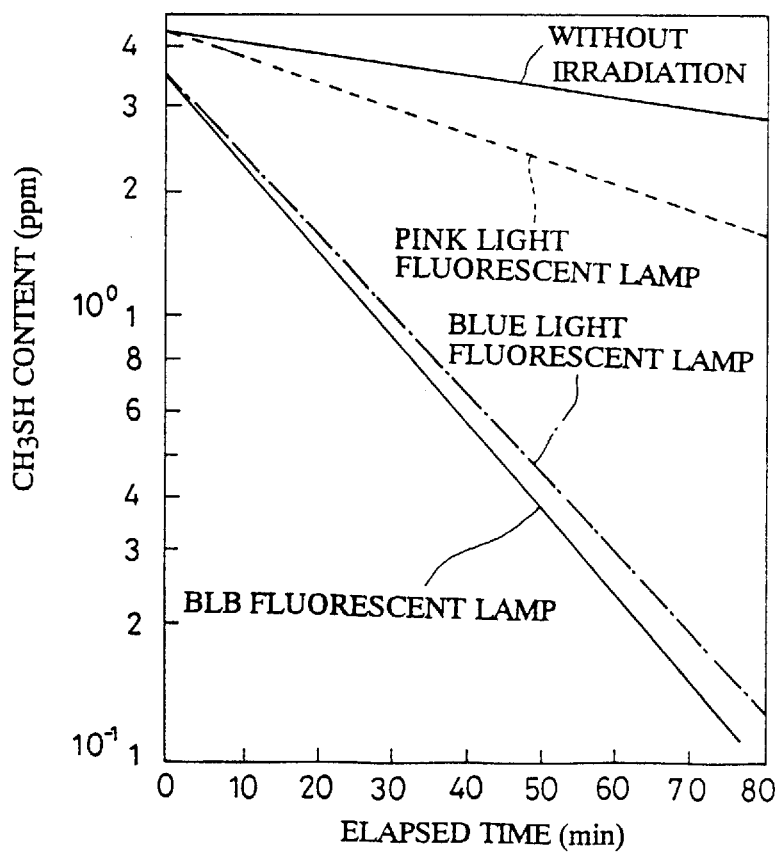
FIG. 9 is a graph showing the variation in the methyl mercaptan content subjected to photodecomposition.

In the graph of FIG. 9, there is shown the variation in the methyl mercaptan content when UV irradiation was carried out by the pink light fluorescent lamp (8 $\mu W/cm^2$ UV intensity), blue light fluorescent lamp (48 $\mu W/cm^2$), and BLB fluorescent lamp (295 $\mu W/cm^2$), respectively. Variation in the methyl mercaptan content taken place without UV irradiation is also shown. It will be noted that the methyl mercaptan content decreases without UV irradiation. It is believed this is because methyl mercaptan is physically absorbed by the $TiO_2$ thin film. From the graph of FIG. 9, it will be understood that, the higher the UV light intensity in the wave length range of 300–390 nm, is the higher is the yield of photodecomposition of methyl mercaptan.

Figure 10:
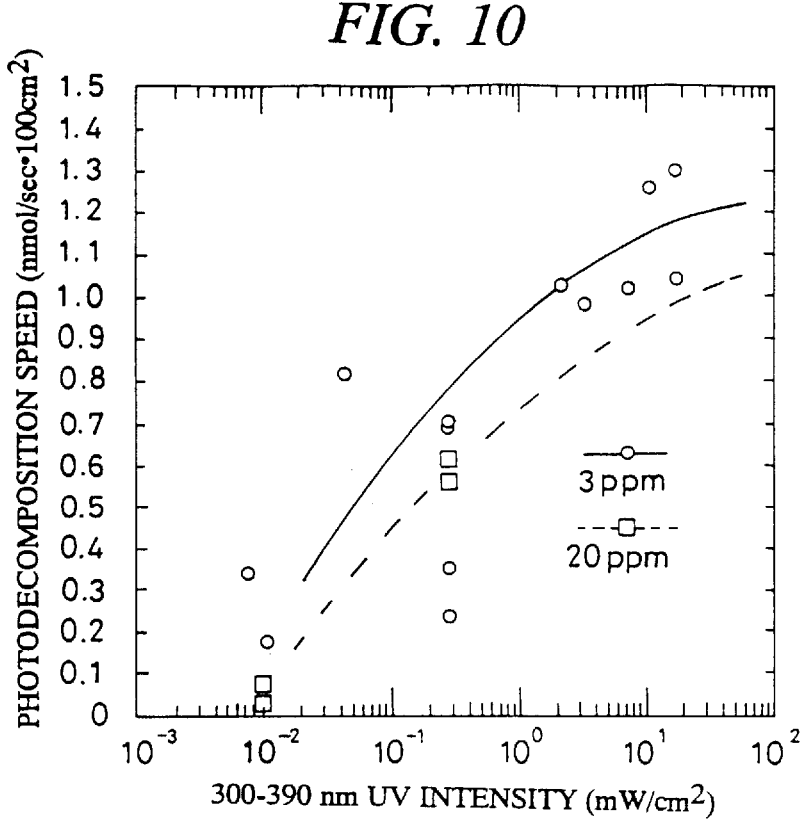
FIG. 10 is a graph showing the speed of photodecomposition of methyl mercaptan under different UV intensities, with the abscissa shown in a logarithmic scale.

The photodecomposition speed of methyl mercaptan was calculated based on the variation in the methyl mercaptan content measured in each run. The results are plotted in the graph of FIG. 10. From the graph, it will be noted that the decomposition speed of methyl mercaptan generally increases with increasing UV intensity. It seemed, however, that the speed of decomposition did not continue to increase even when the UV intensity exceeded 2 $mW/cm^2$. Obviously, this is contrary to the common knowledge and understanding admitted in the prior art that the reaction yield increases as long as the UV intensity is increased.

In an attempt to investigate the cause of this fact, the present inventors have tentatively calculated the quantum yield of photons absorbed by the photocatalyst. To this end, although the number of electrons involved in the decomposition of a molecule of methyl mercaptan is not known with any certainty, the present inventors have presumed that the photodecomposition of methyl mercaptan is a 6-electron process, and sought the quantum yield (%) according to the following equation.

$$\text{quantum yield} = \frac{\text{total number of decomposed CH}_3\text{SH molecules}}{\text{number of photons absorbed by photocatalyst}} \times 6 \times 100$$

Figure 11:
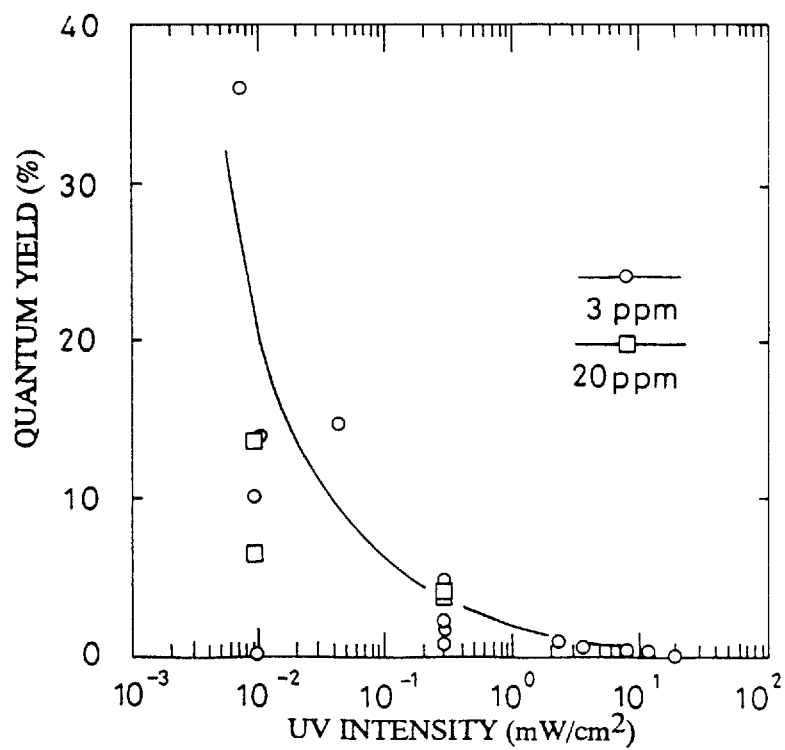
FIG. 11 is a graph showing the quantum yield of photon under different UV intensities, with the abscissa similarly shown in a logarithmic scale.

The results of calculation are plotted in the graph of FIG. 11. As will be apparent from the graph, the present inventors have found that the quantum yield increases with decreasing UV intensity. It was noted that at a UV intensity of 8 $\mu W/cm^2$, a remarkable quantum efficiency as high as about 36% was accomplished.

Figure 12:
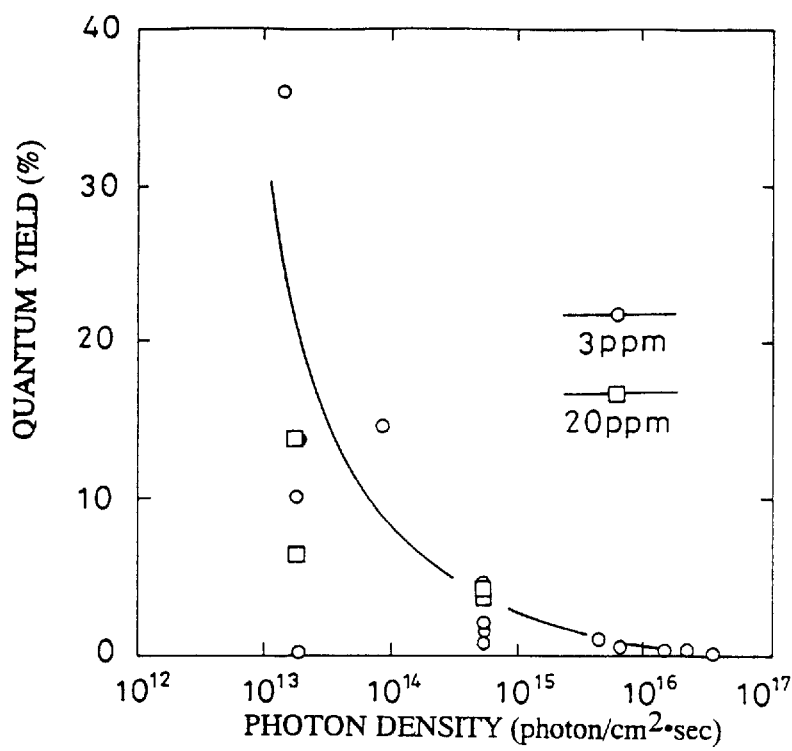
FIG. 12 is a graph similar to FIG. 11, with the UV intensity shown along the abscissa of FIG. 11 being shown here in terms of the photon density.
Figure 13:
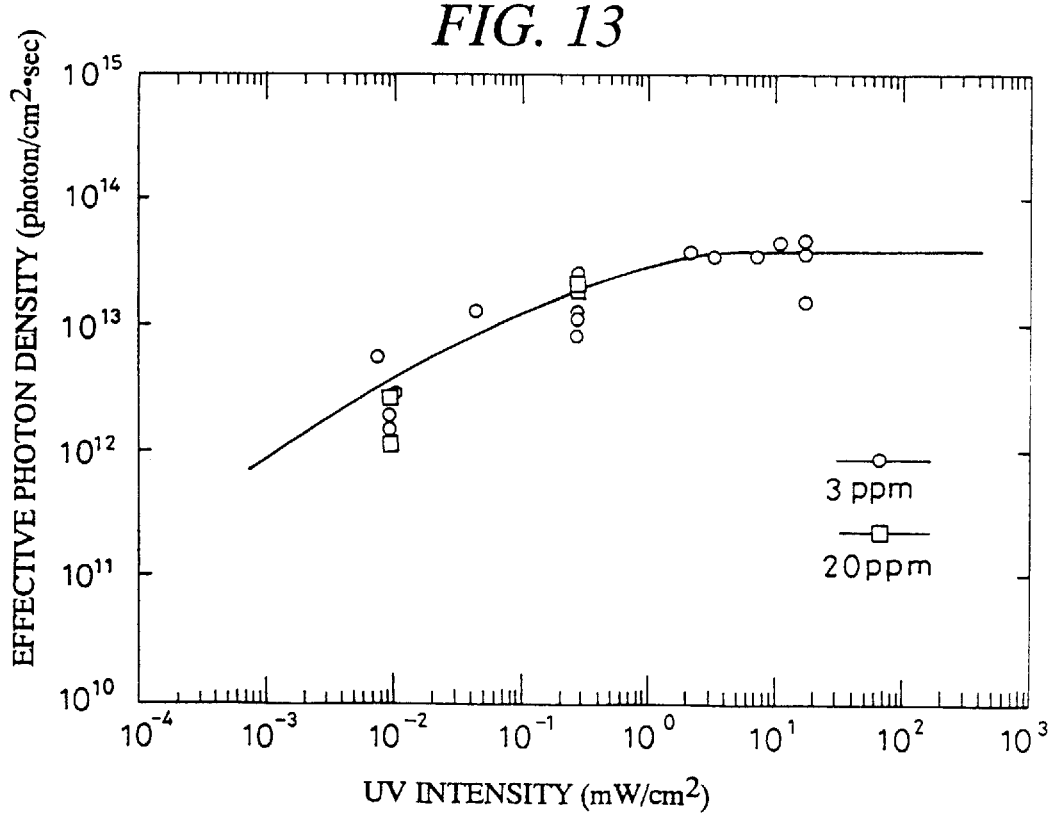
FIG. 13 is a graph showing the effective photon density under different UV intensities, with the abscissa similarly shown in a logarithmic scale.

To ascertain to what degree the photons absorbed by the photocatalyst have actually been effectively utilized in the decomposition of methyl mercaptan, the photon density per second was first computed and then the effective photon density—to be termed as the product of the quantum yield multiplied by the photon density per second and representing the number of photons per unit surface area that have actually contributed to photodecomposition—was calculated based on the photon density per second. The UV intensity shown along the abscissa of FIG. 11 was calculated in terms of the photon density per second and the results are plotted in the graph of FIG. 12. In the graph of FIG. 13, the effective photon density is plotted according to varying UV intensity. The graph of FIG. 13 means that, with the photocatalyst of anatase form $TiO_2$ thin film, the effective photon density attains to the maximum value of $4 \times 10^{13}$ ($photon/cm^2 \cdot sec$) as the UV intensity reaches 2 $mW/cm^2$ and that, thereafter, excessive electrons and holes generated are subject to recombination without contributing to the decomposition of methyl mercaptan even though the UV intensity is increased further.

To compare with the powder system, a ceramic substrate on which powders of anatase form $TiO_2$ were loosely deposited was placed in the desiccator 42 and was tested for photodecomposition of methyl mercaptan by circulating a nitrogen gas containing 3–5 ppm of methyl mercaptan. The results are shown in the following table.

| Light Source (Fluorescent Lamp) | UV Intensity ($\mu W/cm^2$) | Quantum Yield (%) | Effective Photon Density (N/sec · $cm^2$) |
|---|---|---|---|
| White Light | 51.4 | 24.4 | $2.3 \times 10^{14}$ |
| BLB | 1690 | 1.7 | $5.3 \times 10^{14}$ |

As will be apparent from the above table, in the powder system, the effective photon density is on the order of $10^{14}$ which is ten times higher as compared with the thin film system. This means that in the powder system it is desirable to carry out photodecomposition at higher UV intensity.

Figure 14:
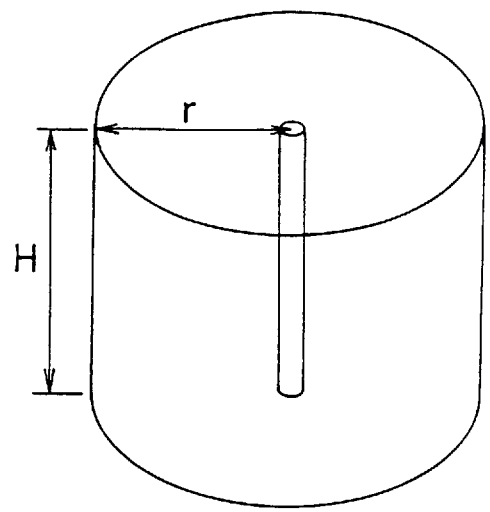
FIG. 14 is a schematic view showing a model of a photocatalytic reactor.
Figure 15:
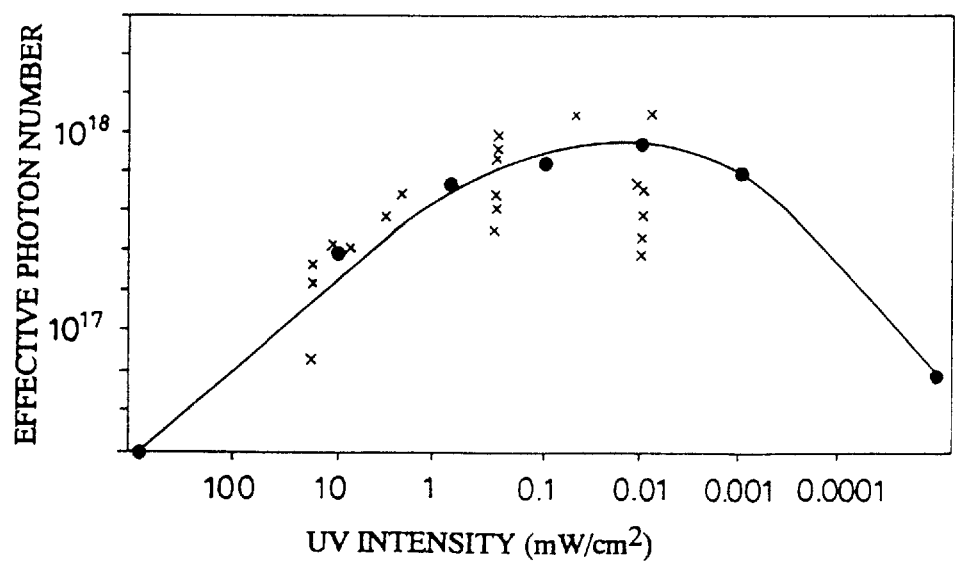
FIG. 15 is a graph showing the variation in the effective photon number as the reactor radius is varied in the model shown in FIG. 14.

Next, the optimum range of UV intensity will be discussed based on the effective photon density shown in the graph of FIG. 13. To this end, a cylindrical reactor model as shown in FIG. 14 will be considered, since a room lined with photocatalytic thin film may be regarded as a photocatalytic reactor. The reactor model has a radius r and a height H (H=1 m) and is provided with a light source arranged at the center thereof and with photocatalyst disposed on the cylindrical inner wall. Assuming that the light source is of a predetermined output, when the reactor radius r is increased, the surface area of the photocatalytic thin film will be increased in proportion to the radius but the UV intensity on the thin film will be decreased roughly in inverse proportion to the square of the distance. The number of effective photons that have actually contributed to the photocatalytic reaction in the reactor as a whole is equal to the product of the effective photon density multiplied by the surface area of the thin film (effective photon number=effective photon density×thin film surface area), whereas the effective photon density varies in response to the change in the UV intensity as shown in the graph of FIG. 13. Assuming that two 40 W BLB fluorescent lamps are used as the light source, the variation in the effective photon number as the reactor radius r is changed was calculated based on the effective photon density shown in FIG. 13. The results are shown in the graph of FIG. 15. As will be understood from this graph, as the UV intensity becomes excessive, the effective photon number, which represents the reaction yield of the reactor as a whole, decreases. This is due to the fact that the quantum yield of photon decreases with increasing UV intensity. The graph of FIG. 15 indicates that the UV intensity range which is most effective from the view point of achieving a high reaction yield of the reactor is 0.001–1 $mW/cm^2$, preferably, 0.01–0.1 $mW/cm^2$.

The relationship between the reaction yield and the electric power consumption in the model of FIG. 14 will be discussed next. Assuming the radius r to be 1 meter and assuming that the wattage of the fluorescent lamps serving as the light source is varied, the lighting efficiency of the fluorescent lamps was calculated according to the following equation.

$$\text{lighting efficiency} = \frac{\text{effective photon number}}{\text{power consumption of lamps}}$$

Figure 16:
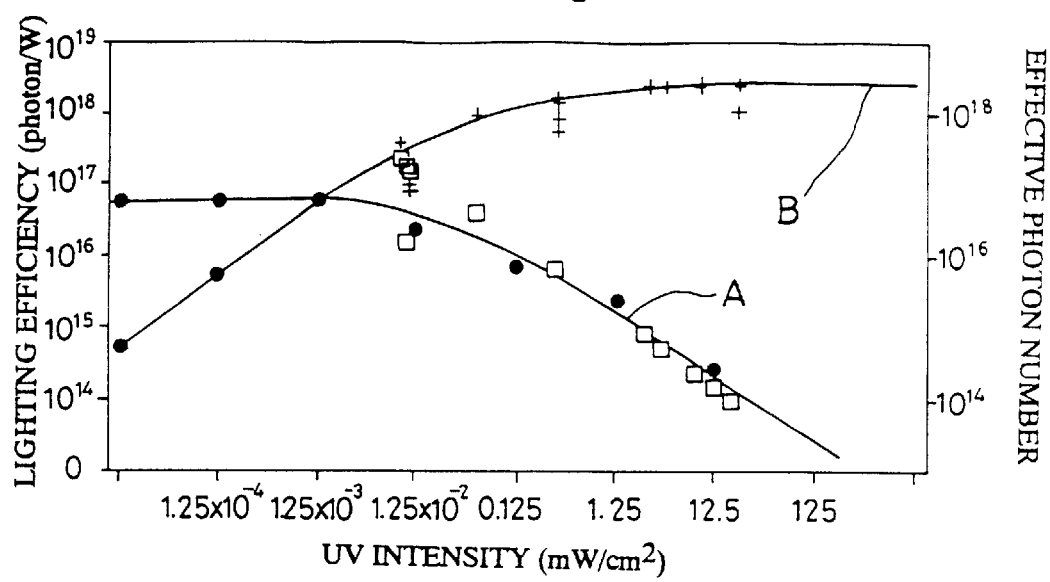
FIG. 16 is a graph showing the variation in the lighting efficiency and the effective photon number as the wattage of the light source is varied in the reactor model of FIG. 14.
Figure 17:
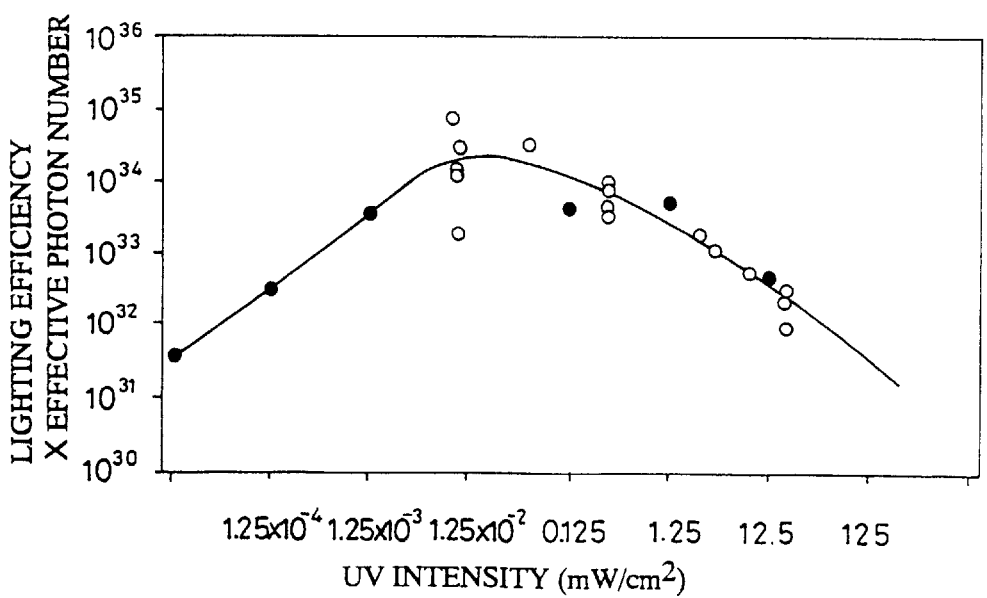
FIG. 17 is a graph showing the variation in the product of the lighting efficiency and the effective photon number shown in FIG. 16.

The lighting efficiency thus obtained is shown by the curve A in the graph of FIG. 16. As the curve A indicates, the number of effective photons per watt of fluorescent lamps decreases with increasing UV intensity. Also shown in FIG. 16 is the effective photon number which is plotted by the curve B. The product of the lighting efficiency multiplied by the effective photon number was calculated and shown in the graph of FIG. 17. It will be noted that the tendency shown in the graph of FIG. 17 is generally consistent with that of FIG. 15. The graph of FIG. 17 indicates that, in order to obtain the maximum reactor yield with least power consumption, it is also desirable to use a UV intensity of 0.001–1 $mW/cm^2$, preferably, 0.01–0.1 $mW/cm^2$.

EXAMPLE 2

Tiles coated respectively with a thin film of anatase form $TiO_2$, similar to that used in Example 1 were tested to examine the sterilizing effect thereof against *Escherichia coli* (W3110 stock). To this end, liquid cultures prepared by shake cultivation for a night were subjected to centrifugal washing and diluted with sterilized distilled water by 10,000 times to prepare bacteria containing liquid. 0.15 ml of the bacteria containing liquid (equivalent to $1-5 \times 10^4$ CFU) was dropped on respective photocatalytic tiles which had previously been sterilized by 70% ethanol and each tile was intimately covered by a glass plate (10×10 cm) to provide a specimen.

In each run, two such specimens were used, with the one subjected to irradiation at varying light intensity, with the other kept in the dark for the purposes of comparison. Irradiation was carried out in such a manner that the UV light intensity in the wave length range of 300–390 nm was 0.8 $\mu W/cm^2$, 1.7 $\mu W/cm^2$, 2.7 $\mu W/cm^2$, 13 $\mu W/cm^2$, 350 $\mu W/cm^2$, 10 $mW/cm^2$, and 20 $mW/cm^2$, respectively. For irradiation at less than 13 $\mu W/cm^2$ intensity, at 350 $\mu W/cm^2$ intensity, and at more than 10 $mW/cm^2$ intensity, a 20-W white light fluorescent lamp (made by Toshiba; FL20SW), a 20-W BLB fluorescent lamp (made by Sankyo Electric; FL20BLB), and a 200-W mercury xenon lamp (made by Yamashita Denso; SUNCURE 202) were used, respectively.

Figure 18:
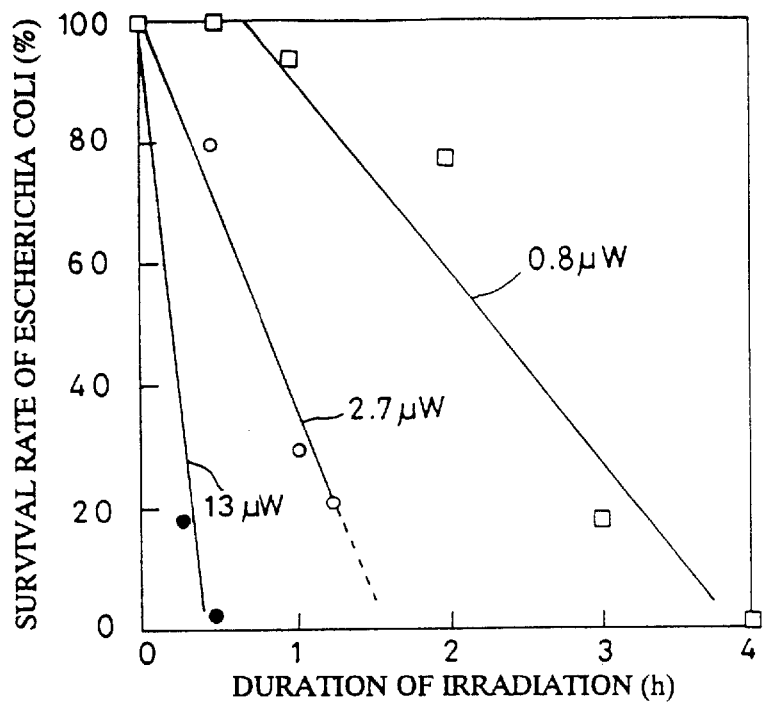
FIG. 18 is a graph showing the survival rate of Escherichia coli subjected to photodecomposition.

After irradiation for a predetermined time, the bacteria containing liquid of both the irradiated specimen and the specimen kept in the dark was wiped with a sterilized gauze and was recovered in 10 ml of physiological saline. The bacteria containing liquid thus recovered was applied for inoculation either on a nutrient agar plate (Nissui Pharmaceuticals) or desoxycholate agar plate (Nissui Pharmaceuticals) and was cultured at 37° C. for a day. Thereafter, the colonies of *Escherichia coli* formed on the culture were counted to obtain the number of bacteria in terms of colony formed unit (CFU). Then, the survival rate of *Escherichia coli* was sought by calculating the ratio of the number of bacteria of the irradiated specimen with respect to that of the specimen kept in the dark. The results are shown in the graph of FIG. 18. This graph shows that, even under a weak UV intensity of as small as 0.8 $\mu W/cm^2$, the number of *Escherichia coli* decreased down to about one tenth upon four hours of irradiation demonstrating that the photocatalyst exhibits a sufficient sterilizing capability required for practical applications.

Figure 19:
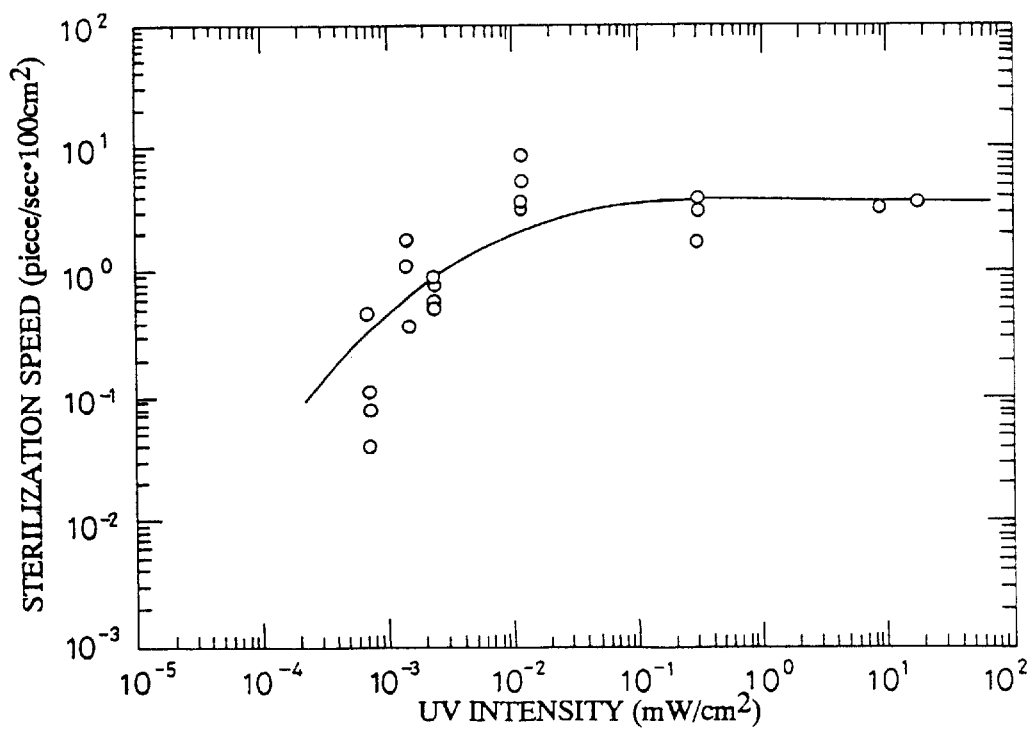
FIG. 19 is a graph showing the sterilization speed for Escherichia coli under different UV intensities, with the abscissa shown in a logarithmic scale.

Then, the speed of sterilization per tile for different UV intensities was calculated from the resulting data and the results are shown in the graph of FIG. 19. It will be noted from the graph that the speed of sterilization reaches to a steady state condition as the UV intensity is increased. Further, the efficiency of sterilization defined by the following equation was calculated for different UV intensities.

sterilization efficiency =

$$\frac{\text{number of } \textit{Escherichia coli} \text{ killed by irradiation}}{\text{number of photons absorbed by the photocatalyst}}$$

Figure 20:
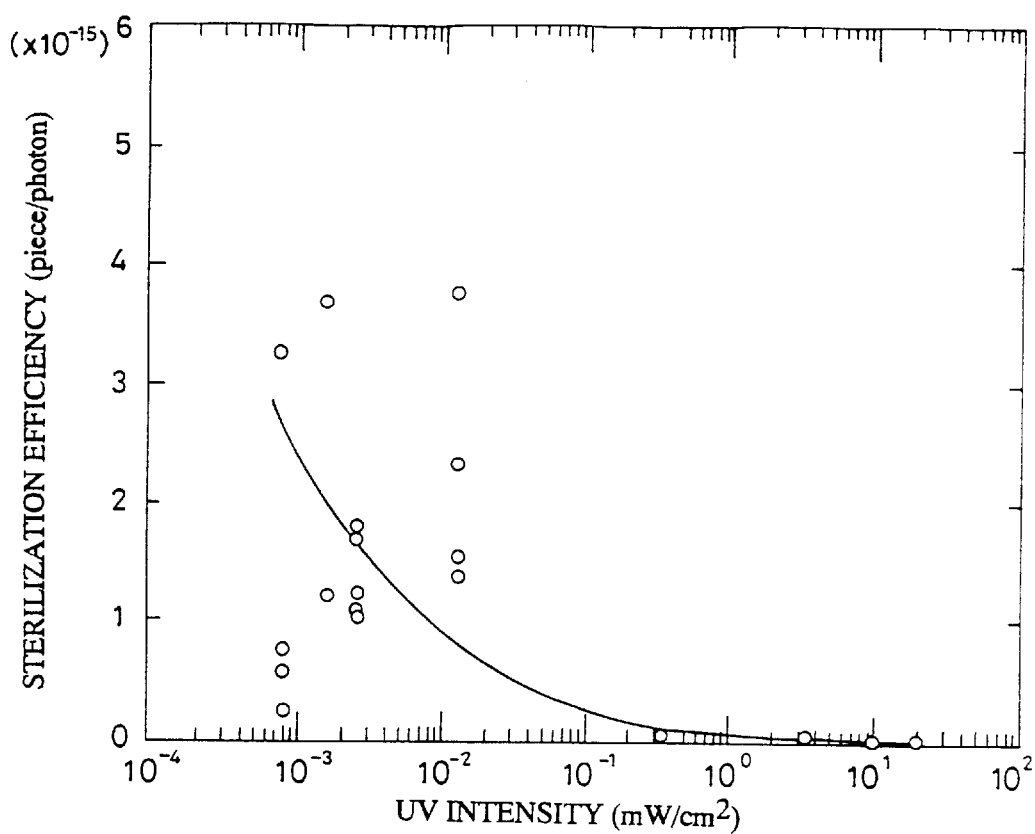
FIG. 20 is a graph showing the sterilization efficiency for Escherichia coli under different UV intensities, with the abscissa similarly shown in a logarithmic scale.

The results are shown in the graph of FIG. 20. It will be noted that this graph is generally in commensurate with the graph of FIG. 11 wherein the quantum yield attained during photo-decomposition of methyl mercaptan is shown and that the number of killed bacteria per photon increases with decreasing UV intensity.

Figure 21:
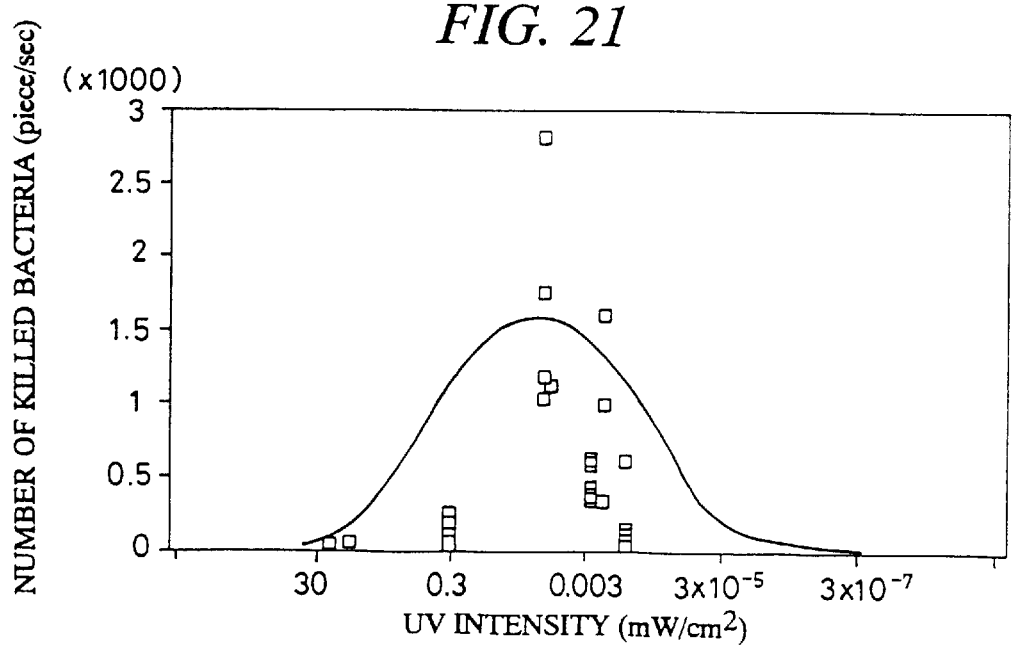
FIG. 21 is a graph showing the variation in the sterilization ability as the reactor radius is varied in the model shown in FIG. 14.

Then, based on the sterilization efficiency thus obtained, the number of bacteria which would be killed each second in the reactor model shown in FIG. 14 was tentatively calculated for varying reactor radius r, assuming that the output of the light source is constant (two 40-W white light fluorescent lamps). The results of calculation are shown in the graph of FIG. 21. From the graph, it will be understood that a high degree of sterilization capability of the reactor will be achieved when the UV intensity is in the range of 0.01–0.1 mW/cm$^2$ or in the vicinity thereof.

We claim:

1. A process for photocatalytically sterilizing a room having an interior defined by enclosing surfaces including vertical walls and a ceiling, comprising:
   covering at least a part of the enclosing surfaces of the room with a thin film of photocatalytic semiconductor material having a band gap energy;
   disposing in the room an electric lamp for emitting visible light with sufficient intensity to illuminate the room with said visible light, said lamp emitting substantially no wavelength component of less than 300 nm and emitting ultraviolet radiation having an energy higher than the band gap energy of said semiconductor material in an amount effective to photoexcite said thin film; and
   energizing said lamp to illuminate said room with visible light and to simultaneously impinge said ultraviolet radiation upon said thin film with an intensity of 0.001–0.1 mW/cm$^2$, to thereby photoexcite said thin film with said ultraviolet radiation whereby bacteria brought into contact with said thin film are photocatalytically destroyed upon illumination of said room.

2. A process according to claim 1, wherein said room is a hospital room.

3. A process according to claim 1, wherein said room is a food processing enclosure.

4. A process according to claim 1, wherein said thin film is impinged by said ultraviolet radiation with an intensity of 0.01–0.1 mW/cm$^2$.

5. A process according to claim 1, wherein said electric lamp is a low-pressure mercury fluorescent lamp capable of emitting light including ultraviolet radiation having wavelengths of about 313 and 365 nm.

6. A process according to claim 1, wherein said electric lamp is a low-pressure mercury fluorescent lamp capable of emitting light including ultraviolet radiation having a wavelength of 350–360 nm.

7. A process according to claim 1, wherein said electric lamp is a high intensity discharge lamp.

8. A process according to claim 7, wherein said high intensity discharge lamp is a metal halide lamp.

9. A process according to claim 1, wherein said electric lamp is an incandescent lamp.

10. A process according to claim 1, wherein said semiconductor material comprises the anatase form of titanium dioxide.

11. A process according to claim 10, wherein the thickness of said thin film is about 0.3–10 micrometers.

12. A process according to claim 10, wherein said thin film of titanium dioxide is supported on a substrate affixed to said enclosing surface.

13. A process according to claim 12, wherein said substrate is a glazed tile.

14. A process according to claim 1, wherein said semiconductor material comprises metalized particles of the rutile form of titanium dioxide.

15. A process according to claim 1, wherein said electric lamp is mounted on said ceiling.

16. A process for photocatalytically decontaminating a room having an interior defined by enclosing surfaces including vertical walls and a ceiling, comprising:
   covering at least a part of the enclosing surfaces of said room with a thin film of photocatalytic semiconductor material having a band gap energy;
   disposing in the room an electric lamp for emitting visible light with sufficient intensity to illuminate the room with said visible light, said lamp emitting substantially no wavelength component of less than 300 nm and emitting ultraviolet radiation having an energy higher than the band gap energy of said semiconductor material in an amount effective to photoexcite said thin film; and
   energizing said lamp to illuminate said room and to simultaneously impinge said ultraviolet radiation upon said thin film with an intensity of 0.001–1 mW/cm$^2$, to thereby photoexcite said thin film with said ultraviolet radiation whereby contaminants brought into contact with said thin film are photodecomposed upon illumination of said room.

17. A process according to claim 16, wherein said thin film is impinged by said ultraviolet radiation with an intensity of 0.01–0.1 mW/cm$^2$.

18. A process according to claim 16, wherein air in the room is deodorized upon photoexcitation of said photocatalytic thin film.

19. A process according to claim 16, wherein airborne organic substances in the room are photodecomposed upon contact with said photocatalytic thin film.

20. A process according to claim 16, wherein said electric lamp is mounted on said ceiling.

21. A process for photocatalytically cleaning a surface of a fixture located in a toilet room, said toilet room having an interior defined by enclosing surfaces including vertical walls and a ceiling, said process comprising:
   covering at least a part of the surface of said fixture with a thin film of photocatalytic semiconductor material;
   disposing an electric lamp in the toilet room for emitting visible light with sufficient intensity to illuminate the toilet room with visible light, for emitting substantially no wavelength component of less than 300 nm and for emitting ultraviolet radiation having an energy higher than the band gap energy of said semiconductor materials in an amount effective to photoexcite said thin film; and
   energizing said lamp to illuminate the toilet room with visible light and to simultaneously impinge said ultraviolet radiation upon said thin film with an intensity of 0.001–1 mW/cm$^2$, to thereby photoexcite said thin film with said ultraviolet radiation whereby contaminants deposited onto said fixture are photodecomposed as said lamp is energized.

22. A process according to claim 21 wherein said electric lamp is mounted on said ceiling.

23. A process for photocatalytically sterilizing a room having an interior defined by enclosing surfaces including vertical walls and a ceiling, said room being equipped with an electric lighting fixture, said lighting fixture being adapted to emit visible light rays for illuminating the room, and to emit ultraviolet radiation having a wavelength not less than 300 nm, said process comprising:

covering a part of the inner wall of said room with a thin film of photocatalytic semiconductor material; and operating said lighting fixture to illuminate said room and to simultaneously impinge said ultraviolet radiation upon said thin film with an intensity of 0.001–1 mW/cm$^2$, to photoexcite said thin film with said ultraviolet radiation and to thereby photocatalytically destroy bacteria deposited on said thin film.

24. A process according to claim 23 wherein said electric lamp is mounted on said ceiling.

* * * * *

UNITED STATES PATENT AND TRADEMARK OFFICE
CERTIFICATE OF CORRECTION

PATENT NO. : 5,874,701          Page 1 of 3
DATED      : February 23, 1999
INVENTOR(S): WATANABE et al It is certified that error appears in the above-identified patent and that said Letters Patent is hereby corrected as shown below:

On the title page, items:

"[75] Inventors", line 2, "Kita-kyushu" should read --Fukuoka--.

"[30] Foreign Application Priority Data", "October 11, 1992" should read --November 10, 1992--.

Under the heading "Foreign Patent Documents", insert:
 --63-267876   11/4/88    JP
   2-280818   11/16/90   JP--.

Under the heading "Foreign Patent Documents", delete the second instance of:
 "4307065   10/1992   Japan
  4407066   10/1992   Japan"

UNITED STATES PATENT AND TRADEMARK OFFICE
CERTIFICATE OF CORRECTION

PATENT NO. : 5,874,701
DATED : February 23, 1999
INVENTOR(S) : WATANABE et al

It is certified that error appears in the above-identified patent and that said Letters Patent is hereby corrected as shown below:

Col. 2, line 30, "group" should read --groups--;
      line 31, "radical" should read --radicals--;
      line 32, "ion" should read --ions--; and
      line 44, "radiations" should read --radiation--.

Col. 5, line 50, after "rather" insert --than--.

Col. 6, line 14, delete "a";
      line 17, after "Also," insert --a--;
      line 47, before "black" insert --a--; and
      line 48, delete "and" insert --or a--.

Col. 7, line 64, after "20C" insert a comma --,--.

Col. 8, line 42, delete "other";
      line 63, delete "[36]" insert --36--.

UNITED STATES PATENT AND TRADEMARK OFFICE
CERTIFICATE OF CORRECTION

PATENT NO. : 5,874,701  Page 3 of 3
DATED : February 23, 1999
INVENTOR(S) : WATANABE et al It is certified that error appears in the above-identified patent and that said Letters Patent is hereby corrected as shown below:

line 25, "radical" should read --radicals--.

Col. 10, line 12, delete "mm, is" and insert --mm is,--.

Col. 12, line 15, after "Example 1" insert a comma --,--; and line 64, delete "to".

Col. 13, line 40, delete "0.1" and insert --1--.

Signed and Sealed this

Eleventh Day of July, 2000

Attest:

Q. TODD DICKINSON

*Attesting Officer*    *Director of Patents and Trademarks*